(12) United States Patent
Lin

(10) Patent No.: US 9,457,199 B2
(45) Date of Patent: Oct. 4, 2016

(54) LIGHT EMITTING TOOTHBRUSH

(71) Applicant: COLGATE-PALMOLIVE COMPANY, New York, NY (US)

(72) Inventor: Hungwei Lin, Lawrence, KS (US)

(73) Assignee: COLGATE-PALMOLIVE COMPANY, New York, NY (US)

(*) Notice: Subject to any disclaimer, the term of this patent is extended or adjusted under 35 U.S.C. 154(b) by 0 days.

(21) Appl. No.: 14/455,382

(22) Filed: Aug. 8, 2014

(65) Prior Publication Data

US 2016/0038762 A1    Feb. 11, 2016

(51) Int. Cl.
| | |
|---|---|
| *A61N 5/06* | (2006.01) |
| *A46B 5/00* | (2006.01) |
| *A46B 15/00* | (2006.01) |
| *A61C 17/34* | (2006.01) |
| *A61C 19/06* | (2006.01) |

(52) U.S. Cl.
CPC ........... *A61N 5/0603* (2013.01); *A46B 5/0095* (2013.01); *A46B 15/0034* (2013.01); *A61C 17/3436* (2013.01); *A61C 17/3481* (2013.01); *A61C 19/066* (2013.01); *A61N 5/062* (2013.01); *A46B 2200/1066* (2013.01); *A61N 2005/063* (2013.01); *A61N 2005/0606* (2013.01); *A61N 2005/0644* (2013.01); *A61N 2005/0652* (2013.01); *A61N 2005/0659* (2013.01); *A61N 2005/0661* (2013.01); *A61N 2005/0662* (2013.01)

(58) Field of Classification Search
CPC .. A61N 5/0603; A61N 5/062; A46B 5/0095; A61C 1/088; A61C 1/12
See application file for complete search history.

(56) References Cited

U.S. PATENT DOCUMENTS

| | | | |
|---|---|---|---|
| 3,667,454 A | | 6/1972 | Prince |
| 3,989,526 A | | 11/1976 | Bissonette |
| 5,030,090 A | * | 7/1991 | Maeda ................. A61C 1/0046 433/216 |
| 5,425,953 A | | 6/1995 | Sintov et al. |
| 5,611,690 A | | 3/1997 | Summers et al. |
| 5,922,307 A | | 7/1999 | Montgomery |
| 5,989,526 A | | 11/1999 | Aaslyng et al. |
| 6,231,343 B1 | | 5/2001 | Ishibashi et al. |
| 6,280,196 B1 | | 8/2001 | Berghash |

(Continued)

FOREIGN PATENT DOCUMENTS

| | | |
|---|---|---|
| EP | 1250896 B1 | 10/2002 |
| EP | 1558166 A1 | 8/2005 |

OTHER PUBLICATIONS

Hydrogen Peroxide and UV Treatment: Melanie Kito, Hi Nguyen, John Tran. Dec. 1998.

(Continued)

*Primary Examiner* — Shay Karls

(57) ABSTRACT

The present invention provides an improved light emitting toothbrush having an angular head removably secured to a base, wherein said base includes an operator for operating the light emitting toothbrush and an electronic power supply for powering said light emitting toothbrush, said angular head adapted for use with a radiation responsive paste applied to a tooth surface for simultaneous removal of bacteria and whitening of the tooth surface a plurality of fiber optic bristles extending from a front brush face of the angular head and in optical communication with a light emitter, said plurality of fiber optic bristles being generally adapted for conducting the emitted radiation from said light emitter towards the tooth surface.

17 Claims, 2 Drawing Sheets

(56) References Cited

U.S. PATENT DOCUMENTS

| | | |
|---|---|---|
| 6,312,670 B1 | 11/2001 | Montgomery |
| 6,322,670 B2 | 11/2001 | Cole et al. |
| 6,322,773 B1 | 11/2001 | Montgomery |
| 6,331,292 B1 | 12/2001 | Montgomery |
| 6,379,653 B1 | 4/2002 | Aaslyng et al. |
| 6,488,914 B2 | 12/2002 | Montgomery |
| 6,514,543 B2 | 2/2003 | Montgomery |
| 6,536,628 B2 | 3/2003 | Montgomery |
| 6,546,628 B2 | 4/2003 | Silverbrook |
| 6,623,272 B2 | 9/2003 | Clemans |
| 6,843,981 B1 | 1/2005 | Ishibashi et al. |
| 6,920,659 B2 | 7/2005 | Cacka et al. |
| 6,920,859 B2 | 7/2005 | Lacka et al. |
| 6,986,883 B2 | 1/2006 | Pellico |
| 7,060,251 B1 | 6/2006 | Elmaleh et al. |
| 7,060,256 B2 | 6/2006 | Pellico |
| 7,086,258 B2 | 8/2006 | Hasegawa |
| 7,086,862 B2 | 8/2006 | Craig |
| 7,094,393 B2 | 8/2006 | Montgomery |
| 7,125,543 B2 | 10/2006 | Hodosh |
| 7,160,111 B2 | 1/2007 | Baughman |
| 7,168,111 B2 | 1/2007 | Bernstein et al. |
| 7,168,122 B1 | 1/2007 | Riddell |
| 7,261,558 B2 | 8/2007 | Rizoiu et al. |
| 7,268,122 B2 | 9/2007 | Zoppetti et al. |
| 7,581,864 B2 | 9/2009 | Craig |
| 8,168,963 B2 | 5/2012 | Ratcliffe |
| 8,215,954 B2 | 7/2012 | Lenne |
| 2007/0111167 A1 | 5/2007 | Russell et al. |
| 2007/0264608 A1* | 11/2007 | Brosnihan .......... A46B 15/0002 433/29 |
| 2008/0060829 A1 | 3/2008 | Jansheski |
| 2011/0296643 A1* | 12/2011 | Shepherd ............. A46B 5/0095 15/167.1 |
| 2013/0089829 A1* | 4/2013 | Boutoussov ......... A61N 5/0603 433/29 |
| 2013/0122467 A1 | 5/2013 | Piergallini et al. |

OTHER PUBLICATIONS

Patent EP1558166A1—Mouthpiece devices and methods to allow uv whitening of teeth.

* cited by examiner

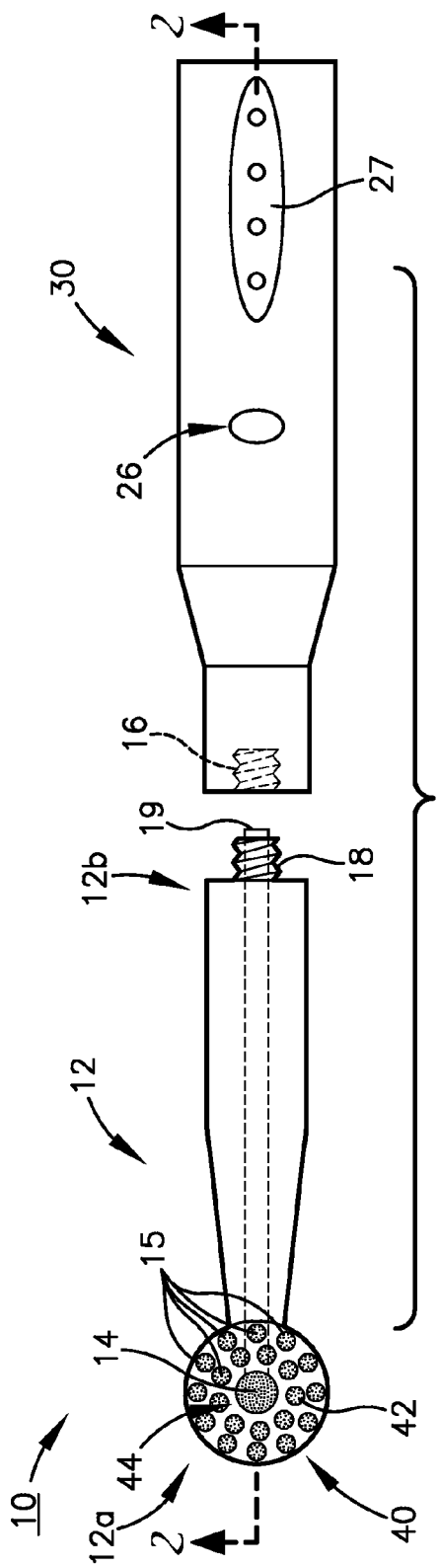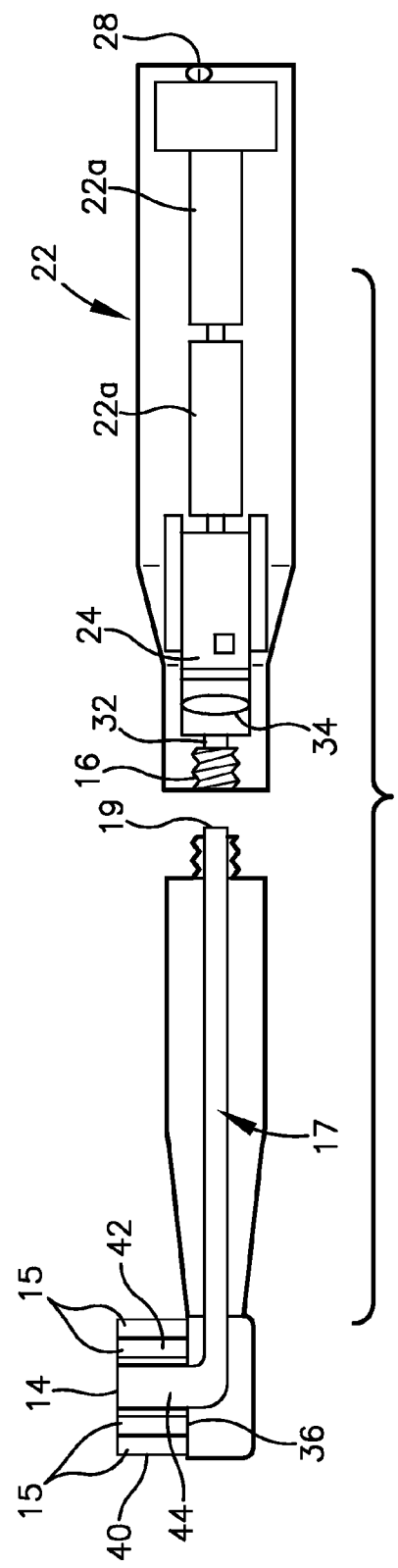

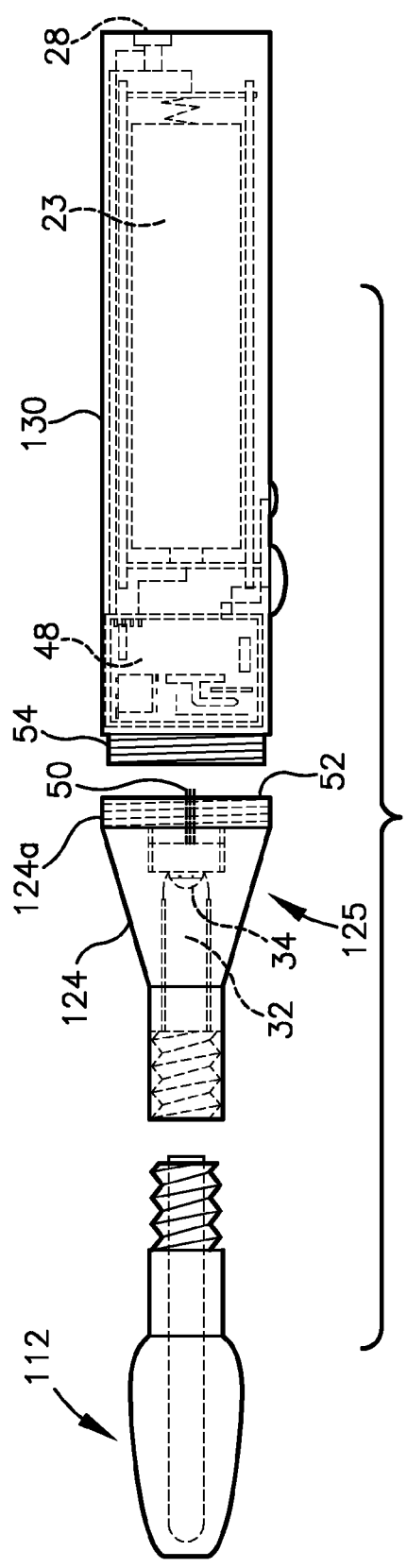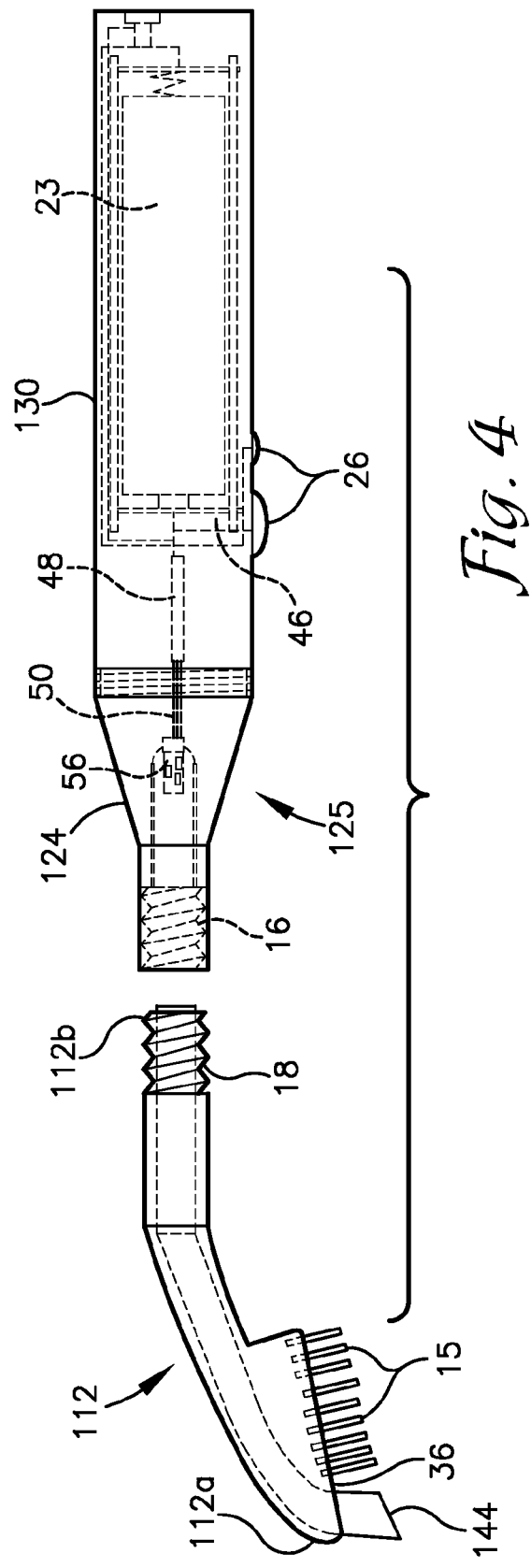

LIGHT EMITTING TOOTHBRUSH

FIELD OF THE INVENTION

The present invention is broadly directed to oral hygienic devices and, more particularly, to an ultraviolet or infrared radiation emitting toothbrush for improved oral hygiene and cosmetic whitening or reducing sensitivity.

BACKGROUND OF THE INVENTION

Teeth whitening and removal of mouth bacteria is a common goal during modern dental procedures. However, regular treatment is required to effectively remove bacteria and effectively whiten teeth. Traveling to the dentist for regular treatments for teeth whitening treatments can be inconvenient and expensive. One way to effectively treat teeth is to use ultra-violet radiation emitted from a specialized dental instrument available for use at a professional dentist's office. Because of the difficulty of visiting a dentist regularly, many people would prefer to utilize a personal dental instrument and products available for residential use rather than travel to the dentist for regular treatment. In-home self-administered treatments are available for whitening teeth such as toothpaste, hydrogen peroxide gel, whitening paint, whitening trays, whitening strips, mouthwash liquid and baking soda. However, in-home dental treatment devices are generally more limited and less effective.

Some professional dental instruments include ultra-violet emitting devices and photosensitizing agents, however, treatment with these devices may cause damage to the gums and teeth to those who lack sufficient training or education on how to use these devices and agents. Possible leakage of whitening agents from the device may cause chronic ingestion of unwanted chemicals. Other in-home treatments with various agents are also available; however, these treatments also have their own limitations and disadvantages, including lack of efficiency, unsatisfying results, prolonged treatment period or prolonged treatment regime which requires excessive time to yield effective results.

For example, some attempts in use of light aided bleaching procedures suffer because the light utilized is emitted from the head of the toothbrush in an indirect manner where it can be reflected or scattered by surrounding fibers or dispersed by bubbles formed during the brushing process or from overly dispersed bristle configuration which limit the concentration of the emitted radiation and therefore are limited from energizing the radiation reactive agent on the intended area. Others attempts include the use of trays or mouthpieces which provide only limited radiation to the front and not upon the rear of the tooth surface thereby reducing the treatments effectiveness.

Therefore, there is a need to provide a light emitting toothbrush which provides a high intensity ultraviolet or infrared radiation with a concentrated radiation geometry directly to the tooth surface and the hard to reach proximal surface between the teeth to enhance tooth whitening, bacteria disinfection or sensitivity reduction while providing mechanical abrasion for removal of food particles in conjunction with proper toothpaste or dental gel using the combination of optical and non-optical brushing bristles in an at-home, easily transportable, waterproof, head replaceable light emitting toothbrush.

SUMMARY OF THE INVENTION

The present invention is an improved uv-radiation or infrared emitting toothbrush with a uv-reactive whitening or sensitivity reduction agent and method of whitening teeth and treating bacteria, soothing tooth sensitivity. The toothbrush comprises an angled head having a plurality of fiber-optic bristles affixed to a first side with a male structure associated with a second side of the head and adapted for receipt by a threaded receiver associated with a handle including an operator, a light emitter and power source. The bundle of fiber-optic bristles also operates as a light guide extending between the light and power source through the male structure for optical communication with a light guide receiver associated with the threaded receiver, the light guide providing radiation generated by the light source through the light guide to the angled head. Optionally, the light source selectively alternates the provided radiation transmitted directly to the tooth surface, the radiation having a range of desired wavelengths for activation of the whitening or sensitivity soothing agent applied at a desired tooth surface upon contact with the optical bristles.

Various objects and advantages of the present invention will become apparent from the following description taken in conjunction with the accompanying drawings wherein are set forth, by way of illustration and example, certain embodiments of this invention. The drawings submitted herewith constitute a part of this specification, include exemplary embodiments of the present invention, and illustrate various objects and features thereof.

BRIEF DESCRIPTION OF THE DRAWINGS

FIG. 1 is an exploded plan view of an embodiment of the present invention.

FIG. 2 is cross-sectional side elevation of the embodiment of FIG. 1.

FIG. 3 is a cross-sectional bottom view of an alternative embodiment of the present invention.

FIG. 4 is a cross-sectional side perspective of the alternative embodiment of FIG. 3.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 10 (FIGS. 1-2) generally designates an embodiment of the light emitting toothbrush for enhancing the performance of tooth whitening and bacteria killing when used along with a radiation responsive material (not shown) such as a paste or gel. The light emitting toothbrush 10 comprises an angled head 12 with a first side 12a separated from a second side 12b with a plurality of fiber bristles 14 extending therebetween. The fiber bristles are comprised of a core separated by a sheath fabricated from an optically transparent material such as extruded glass, silica or plastic with the sheath having a lower index of refraction than the core and presenting a reflective surface for maintaining the transmitted radiation in association with the core and as such is adapted for transmitting the emitted radiation from the light emitter 24 to the tooth surface. In the illustrated embodiment of FIGS. 1-2, the fiber bristles 14 are adapted for optical communication with a light emitter 24, conducting the emitted radiation from the light emitter 24 towards the tooth surface for radiating the radiation responsive material.

The direct emission of radiation upon the tooth surface not only accelerates tooth whitening but also can be used to reduce tooth sensitivity. Infrared irradiance alone or in combination with fluoride or nitrate based chemicals may provide an improved method for treating tooth sensitivity. In both cases, the emitted radiation may accelerate the chemical reactions based upon the energy, density and area of exposure to the emitted radiation.

While, the angled head 12 configuration depicted in FIGS. 1-2 include a plurality of optical bristles 14 and non-optical bristles 15 arranged with a plurality of cylindrical columns arranged in an outer ring 40, an inner ring 42 and a central column 44 all being concentric with the central column having a plurality of fiber optical bristles 14. The central column 44 includes a plurality of fiber optical bristle which for example, may include but is not limited to 100 to 200 strands of 0.20 mm optical fibers with a 4-5 mm diameter. The fiber optic and non-optical bristles are adapted for abrading a tooth surface (not shown) while the optical fiber bristles also emit radiation upon the radiation responsive material. In this way, the fiber bristles may overcome any air pockets formed during the brushing process and maintain contact with the radiation reactive agent at the tooth surface. Other known angled head 12 configurations which achieve the same features as those mentioned above are considered within the scope of the present invention.

The angled head includes a central shaft for extending the fiber optic bundle 17 towards the second side 12*b* associated with a male structure 18 and presenting the fiber optic bristles 14 for optical connection with the light emitter by way of an optical socket 16 having a threaded configuration. The fiber optic bundle 17 may extend through a manifold 36 associated with a front face of the brush and may include a plurality of thin gauge optical fibers 14 (less than 0.25 mm in diameter) which may be grouped into a 4-6 mm diameter fiber optic bundle 17 with the central column 44 being spread into brushing bristles and shaped for the optimal light distribution and abrasion.

Alternatively, the male structure 18 may be associated with a base 30 and an optical socket 16 may be associated with the second side 12*b* of the angled head 12. The male structure 18—optical socket 16 combination provides for an easily removable, securable connection between the angled head 12 and base 30 allowing for rapid detachment of the angled head 12 from the base 30. In the illustrated embodiment, the base 30 includes the light emitter 24, an operator 26, an indicator 27, a charging port 28 in electric communication with a power source 22 which may utilize known power sources such as traditional batteries or rechargeable batteries such as Ni—ca, Ni-MH or Li-ion composition batteries.

In the illustrated embodiment, the angled head 12 is removably secured to the base 30 with the optical fiber bundle 17 being presented at the male structure 18. One feature of the present invention is that the angled head 12 is easily removable from the base 30 for transport, storage or replacement. A fiber optic connector 19 is provided within the angled head 12 at an optically conductive surface adapted for connection to the base 30 which provides for optical communication between the angled head 12 and the base 30. In this embodiment, a first optically conductive surface associated with the angled head 12 is positioned adjacent to or sufficiently near a second optically conductive surface associated with the base 30 such that there is a minimal gap between the first and second optically conductive surfaces to allow for sufficient transmission of the emitted radiation from the light emitter 24 to the tooth surface.

In the illustrated embodiment, an optical fiber connector 19 is presented by the male structure 18. The optical fiber connector 19 couples and aligns the contained plurality of optical fibers 14. The optical fiber connector 19 may include known connector configurations such as bayonet, screw, clip, snap or push-pull type, although the illustrated connector is a screw type connector which may be rated for between 500 and 1,000 mating cycles. In addition, the first optically conductive surface of the angled head may include a polished surface with a slightly curved surface to facilitate improved optical communication or fiber connectivity. As illustrated, the optical fiber connector 19 allows for improved receipt and transmission of the emitted radiation through the angled head 12 to the tooth surface during receipt of the male structure 18 by the optical socket 16.

The base 30 also includes an operator 26 which may control a number of different features such as rotation, speed, light or vibration which may be provided through a variable speed brush oscillator, a variable or fixed frequency light emitter, or a variable speed or fixed speed vibrator to provide different operational characteristics. In addition, an indicator 27 may be provided to indicate which operational mode has been selected or to provide a timing or speed or operating indicator for the convenience of the user.

FIG. 2 illustrates the fiber bundle 17 which extends from the optical connector associated with the head to the central column 44. In addition, the light emitter 24 is illustrated within the base 30 with an optical channel 32 extending from the light emitter 24 to the optical socket 16 with the optical channel 32 presenting a first optically conductive surface in association with the base 30 for transmission of the emitted radiation to the angled head 12. In FIG. 2, the second optically conductive surface of the angled head 12 is the male structure 18 while the first optically conductive surface of the base 30 is the optical channel 32 extending from light emitter 24 and along a base of the optical socket 16. The fiber optic connector 19 provides a termination for the plurality of fiber bristles 14 contained within the fiber optic bundle 17 while mechanically coupling and aligning the optical fibers 14 for receipt of the emitted radiation (not shown).

The light emitter 24 may be comprised of at least 3 integrated circuits having high power LEDs with a power rating of between 1-10 w depending on the desired radiation characteristics. For example, the light emitter 24 may utilize a blue or ultraviolet LED to generate radiation within the 280-550 nm, or 650-1000 nm using a red or infrared LED. Alternatively, a variety of removable light emitters 124, as illustrated in FIGS. 3-4 may be utilized to provide different radiation characteristics such as a different wavelength or frequency as desired by the user.

A charging port 28 is also illustrated in FIGS. 3-4 for electrical connectivity with an external 5VDC, for example, power supply for charging or operating the base 30. In addition, the rechargeable batteries 22*a*, which may be lithium-ion batteries rated for 3.7v, in the illustrated embodiment provide the necessary power supply 22 for operation of the light emitting toothbrush 10 during portable use.

FIG. 2 also illustrates a focal lens 34 is illustrated in association with the light emitter 24 to impact the characteristics of the emitted radiation. In an alternative embodiment, the focal lens 34 may be contained within the male structure 18 associated with the angled head 12 and arranged to provide the desired illumination characteristic such as spreading the light within the fiber optic bundle 17. The focal lens 34 can act as a filter or act as a magnifier to control which and what radiation is emitted during operation. For example, the emitted radiation may include radiation outside the desired range and in some cases may actually be harmful. Prolonged or repeated exposure to this radiation may cause injury or damage to the tooth surface or user. In addition, the focal lens 34 may be adjusted, electronically or mechanically to adjust the emitted radiation characteristics from the light emitter 24. In addition, a heat sink may be provided which may simply be a stainless steel metal block for absorbing any excess heat and prevent over-heating of the various components which may be housed within the base 30, such as the electronic circuit or light emitter 34.

FIG. 2 also illustrates the fiber optic bundle 17 extending along the central shaft of angular head 12 with the fiber optic bundle 17 spreading spatially outward as it extends through a manifold 36. The manifold 36 secures and positions both the plurality of optical and non-optical bristles 14, 15 for direct contact with the tooth surface such as when the head 12 is used to apply and spread the radiation reactive agent (not shown) during brushing. The manifold 36 may have a plurality of configurations for orientating, receiving and extending the optical and non-optical fiber 14, 15 bristles. FIG. 2 illustrates a generally parallel and vertical bristle orientation.

The radiation reactive agent (not shown) for treating bacteria and teeth whitening may take advantage of photo-bleaching effects known to those skilled in the art. Common bleaching compositions may include a liquid, paste or gel and is applied to the tooth surface with the bristles of the toothbrush 10. Some exemplary photo-bleaching compositions may include a peroxide based material such as but not limited to, but is not limited to, hydrogen peroxide, carbamide peroxide, carbamyl peroxide, calcium peroxide, sodium percarbonate, perhydrol urea and peroxy-acetic acid in combination with a photo-sensitizer and with or without dyes, fragrances, flavors or titanium dioxide. In addition, a sodium nitrate based toothpaste may be used with for example, radiation emitted from a light emitter including a red LED for therapeutic use.

During operation, the radiation reactive agent is applied to the bristles and then to the teeth where radiation having the desired characteristics is generated within the light emitter 24 and transmitted through the optical channel 32 associated with the optical socket 16 to the optical connector 19 associated with the male structure 18 engaged by the optical channel 32 for transmission of the emitted radiation along the fiber optic bundle 17 through a central column 44 extending away from a top facing surface of the angled head 12 for direct contact with the tooth surface in receipt of the applied radiation reactive agent. Using the manifold 36, also referred to herein as a front brush face, the central column 44 can deliver high intensity light anywhere within the cavity of the mouth and the plurality of bristles optical and non-optical 14,15 can be used to distribute the radiation reactive agent simultaneous to the transmission of radiation to the tooth surface.

FIGS. 3-4 illustrate an alternative embodiment of the angled head 112 having an alternative configuration, with the fiber optic bundle 17 located near the first side 112*a* with the central column 44 extending forwardly and outwardly from the front brush face, the non-optical fibers 15 spaced along the front brush face 36 and extending from the angularly tapered central column 144 towards the alternative second side 112*b*. In this way, the alternative angled head 112 allows for placement of the optical bristles 14 within the most inner part of the teeth in order to emit light onto the most inner portion of the oral cavity including towards the inwardly positioned teeth and gums. In addition, the fiber optic bundle 17 is illustrated as being shaped with a shaped or slanted contour consisting of various lengths of fiber optic bristles in order to maintain intimate contact between the fiber optic bristles and the tooth surface for optimal light contact and spreading performance. Generally, the intensity and area of light disposal by the fiber optic bundle 17 can be equivalent to a similar intensity of light exposure by a dental curing light or dental laser light illuminating the tooth surface.

FIGS. 3-4 also illustrate an alternative light emitter 124 which is illustrated as being removable from the base 130, the power supply 23, the charging port 28, an electrical circuit for selectively operating the light emitter 124 using, for example a plurality of operators 26 positioned along the exterior sidewall of the base 130 to control the light emitter 124.

As illustrated the alternative light emitter 124 includes a light emitter housing 125 with a first housing end 124*a* having an electrical connection 50 for electric communication with the electrical circuitry 48 and a mechanical connection 52 for securing the first housing end 124*a* of the light emitter 124 to a complementary mechanical structure 54 associated with the base 130. The illustrated connection located between the mechanical connection 52 and complementary mechanical structure 54 is threaded, but other mechanical connections are generally known and are considered within the scope of the present invention. The base 130 is illustrated with an oscillating structure 46 powered by the power source 23 for providing vibration motion during operation to enhance the mechanic abrasion action.

The electrical connection 50 includes electrically conductive materials which are adapted for contact with the electrical circuitry 48 extending from the power source. The electrical circuit 48 provides desired electrical energy for operatively energizing the light emitter 124. The emitter 124 may be selectively designed for varying energy levels based upon the desired operation or desired emitted radiation, or alternatively, may be substituted with varying designed emitters 124 having alternative operational characteristics. In addition, the electrical circuitry 48 may include timer control circuitry (not shown) or thermal control circuitry (not shown) to control the operating time or operating temperature and limit over-heating operation of the light emitter 124. Alternatively, the electrical circuitry 48 may be housed within the light emitter housing with a power connection being provided for contact with the base 130. The alternative light emitter 130 is contained within the removable housing structure and extends between the base 130 and the head 112. A second housing end 124*b* presents the optical socket 16 for connectivity with the fiber optic connector 19 extending outwardly from head 112 at the second side 112*b* associated with the male structure 18. The focal lens 34 is illustrated in FIG. 2 presented at one end of optical channel 32 which receives the emitted radiation and transports it toward the optical socket 16 which is recessed within the light emitter housing 125. In addition, a plurality of LED's 56 are shown in FIG. 4 in association with the light emitter 124. The LED's 56 may produce radiation within a specific range or a variety of ranges, as desired to produce radiation within the interested range of wavelengths, for example to accelerate either an oxidation or whitening reaction or mineral precipitation with the applied reactive agent. In addition, the light intensity may be adjusted as desired based upon the user's preference or desired spectrum.

By way of example the interchangeable light emitter 124 may utilize a blue or UV LED to generate radiation within the range of 280-550 nm to accelerate the whitening action and produce oral sanitations or deodorization when used with the radiation reactive agent containing, for example and not as a limitation, a peroxide based oxidizer such as hydrogen peroxide, calcium peroxide, cumene peroxide or carbamide peroxide. The same or a substitute light emitter 124 may also utilize a red/infrared LED to generate radiation within the range of 650-1000 nm to enhance the performance of tooth desensitization when coupled with a radiation reactive agent containing a nitrate or fluoride based product such as sodium nitrate or sodium fluoride. In some cases the interchangeable light emitter 124 may provide dual functionality to achieve the desired effect, such as emitting multiple frequencies.

The light emitter 24 consists of an integrated circuit which in one embodiment includes at least one light emitting diode such as an ultraviolet light emitting diode capable of handling 50 mV-10 W of power to produce radiation having the desired characteristics for transmitting the emitted radiation from the light emitter 24 through the optical socket 16 which is in receipt of the male structure 18 presenting the fiber optic bundle 17 for transmitting the emitted radiation to the tooth surface. In one embodiment, the emitted radiation will be within the blue to violet spectrum, in another it may be 280 nm, 365 nm, 405 nm, 440 nm or 550 nm within the ultra-violet spectrum and consistent with "cool," low temperature radiation.

It is to be understood that while certain forms of the present invention have been illustrated and described herein, it is not to be limited to the specific forms or arrangement of parts described and shown.

What is claimed and desired to be secured by Letters Patent:

1. A light emitting toothbrush comprising:
   a head removably secured to a base, wherein said base includes an operator for operating the light emitting toothbrush and an electronic power supply for powering said light emitting toothbrush;
   a plurality of fiber optic bristles arranged in a tuft extending from a front brush face of the head and in optical communication with a light emitter, said plurality of fiber optic bristles being generally adapted for conducting radiation emitted from said light emitter towards a tooth surface;
   a focal lens in association with the light emitter to impact a characteristic of the radiation emitted from the light emitter, wherein the focal lens is adjustable to adjust the characteristic of the radiation emitted from the light emitter;
   said plurality of fiber optic bristles grouped into a fiber optic bundle which extends along a central shaft of the head with the plurality of fiber optic bristles spacing outwardly through a manifold;
   an optical socket in optical communication with said fiber optic bundle and said light emitter;
   an optical channel extending from said light emitter for connection to said optical socket for transmitting the emitted radiation from said light emitter housed by said base to said head; and
   said manifold securely arranging a plurality of non-optical bristles and said fiber optic bristles whereby said plurality of fiber optic bristles and said plurality of non-optical bristles collectively abrade the tooth surface while emitting radiation thereto.

2. The light emitting toothbrush of claim 1 wherein said optical socket has a threaded configuration.

3. The light emitting toothbrush of claim 1 wherein said fiber optic bundle extends through said manifold and said fiber optic bristles are thin-gauge optical fibers.

4. The light emitting toothbrush of claim 1 further comprising a plurality of tufts of bristles extending from the front brush face of the head, the plurality of tufts of bristles including a plurality of tufts consisting of the non-optical bristles and at least one tuft consisting of the fiber optic bristles, wherein said plurality of tufts of non-optical bristles form an outer ring of tufts and an inner ring of tufts each surrounding the tuft of fiber optic bristles, the tuft of fiber optic bristles is centrally located on the front brush face of the head, and the inner and outer rings of tufts are concentric with the tuft of fiber optic bristles.

5. The light emitting toothbrush of claim 1 wherein said optical socket is associated with said head.

6. The light emitting toothbrush of claim 1 further comprising a fiber optic connector within said head at an optically conductive surface.

7. The light emitting toothbrush of claim 6 wherein said optically conductive surface provides optical communication between the head and the base.

8. The light emitting toothbrush of claim 6 wherein said fiber optic connector is presented by a male structure adapted for receipt by the optical socket, the fiber optic connector optically coupling and aligning a proximal end of the plurality of fiber optic bristles.

9. The light emitting toothbrush of claim 6 wherein said fiber optic connector has a bayonet configuration.

10. The light emitting toothbrush of claim 1 further comprising an optical channel extending from said light emitter to said optical socket.

11. The light emitting toothbrush of claim 1 wherein said light emitter includes at least one high power LED.

12. The light emitting toothbrush of claim 1 wherein said light emitter provides at least two functions.

13. The light emitting toothbrush of claim 1 wherein the focal lens acts as a filter to control a wavelength of the radiation emitted towards the tooth surface.

14. The light emitting toothbrush of claim 1 wherein said focal lens is a light focusing lens.

15. The light emitting toothbrush of claim 1 wherein said fiber optic bundle extends through said manifold and said fiber optic bristles are thin-gauge optical microfibers.

16. A light emitting toothbrush comprising:
   a handle;
   a head attached to the handle;
   a light emitter located in the handle or the head;
   a plurality of tufts of bristles extending from the front face of the head, the plurality of tufts of bristles including at least one tuft consisting of a plurality of fiber optic bristles and a plurality of tufts consisting of non-optical bristles;
   wherein the plurality of fiber optic bristles are in optical communication with the light emitter, said plurality of fiber optic bristles adapted for conducting radiation emitted from said light emitter to an oral care surface of a user;
   wherein said plurality of tufts of non-optical bristles form an outer ring of tufts surrounding the tuft of fiber optic bristles; and
   wherein said plurality of tufts of non-optical bristles form an inner ring of tufts surrounding the tuft of fiber optic bristles, the inner ring of tufts surrounded by the outer ring of tufts, the inner and outer rings of tufts being concentric with the tuft of fiber optic bristles.

17. A light emitting toothbrush comprising:
a handle;
a head attached to the handle;
a light emitter located in the handle or the head;
a plurality of tufts of bristles extending from the front face of the head, the plurality of tufts of bristles including at least one tuft consisting of a plurality of fiber optic bristles and a plurality of tufts consisting of non-optical bristles;
wherein the plurality of fiber optic bristles are in optical communication with the light emitter, said plurality of fiber optic bristles adapted for conducting radiation emitted from said light emitter to an oral care surface of a user;
wherein the tuft of fiber optic bristles is located at a distal end of the head and is a distal-most tuft on the head.

* * * * *